(12) United States Patent
Kono et al.

(10) Patent No.: US 8,323,197 B2
(45) Date of Patent: Dec. 4, 2012

(54) BLOOD FLOW MEASURING AND EVALUATING APPARATUS

(75) Inventors: Miyuki Kono, Kokubunji (JP); Takashi Azuma, Kodaira (JP); Shin-ichiro Umemura, Sendai (JP); Hiroki Tanaka, Musashino (JP)

(73) Assignee: Hitachi, Ltd., Tokyo (JP)

( * ) Notice: Subject to any disclaimer, the term of this patent is extended or adjusted under 35 U.S.C. 154(b) by 586 days.

(21) Appl. No.: 12/039,344

(22) Filed: Feb. 28, 2008

(65) Prior Publication Data

US 2008/0306383 A1  Dec. 11, 2008

(30) Foreign Application Priority Data

Jun. 11, 2007  (JP) .................. 2007-153491

(51) Int. Cl.
*A61B 8/00* (2006.01)
(52) U.S. Cl. ........................ 600/438; 600/455
(58) Field of Classification Search .................. 600/421, 600/423, 437, 442, 446, 453, 455, 459, 462, 600/463, 478; 73/584
See application file for complete search history.

(56) References Cited

U.S. PATENT DOCUMENTS

| | | | | |
|---|---|---|---|---|
| 4,660,564 A | * | 4/1987 | Benthin et al. | 600/449 |
| 4,922,909 A | * | 5/1990 | Little et al. | 600/300 |
| 5,706,818 A | * | 1/1998 | Gondo | 600/447 |
| 6,741,730 B2 | * | 5/2004 | Rahn et al. | 382/131 |
| 2005/0015009 A1 | * | 1/2005 | Mourad et al. | 600/438 |
| 2006/0122489 A1 | * | 6/2006 | Kato et al. | 600/411 |
| 2006/0211942 A1 | * | 9/2006 | Hoctor et al. | 600/438 |
| 2006/0276695 A9 | * | 12/2006 | Lynn et al. | 600/300 |
| 2007/0088215 A1 | * | 4/2007 | Thomas Dubberstein et al. | 600/437 |

FOREIGN PATENT DOCUMENTS

JP  2005-110724  4/2005

OTHER PUBLICATIONS

"A Point Process Approach to Assess the Frequency Dependence of Ultrasound Backscattering by Aggregating Red Blood Cells" by Savery, et al.

* cited by examiner

*Primary Examiner* — James Kish
*Assistant Examiner* — Michael N Fisher
(74) *Attorney, Agent, or Firm* — Mattingly & Malur, PC

(57) ABSTRACT

Means for measuring and evaluating a dynamic property of a blood flow in a superficial blood vessel of a living body are constructed.

A physical stimulus is given to the blood flow, and an ultrasonic response from the blood flow to the physical stimulus is measured and evaluated, which allows the blood property to be evaluated noninvasively and dynamically. Therefore, a medical check and a lifestyle-related diseases prevention effect are promising.

8 Claims, 16 Drawing Sheets

FIG. 2
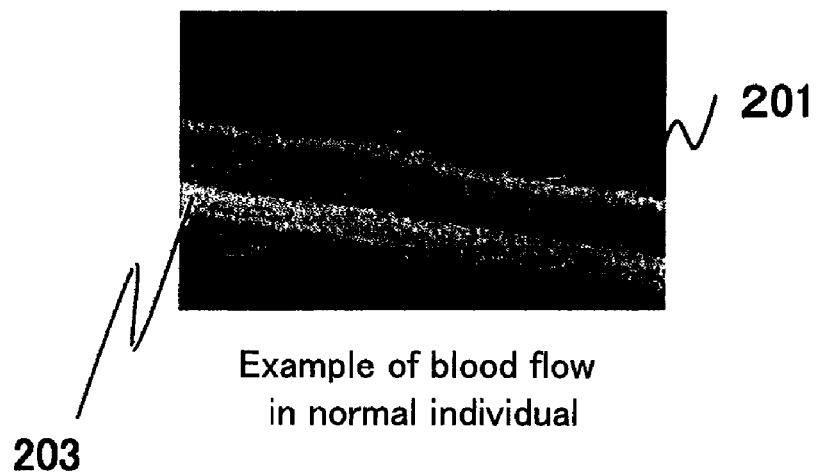
Example of blood flow
in normal individual
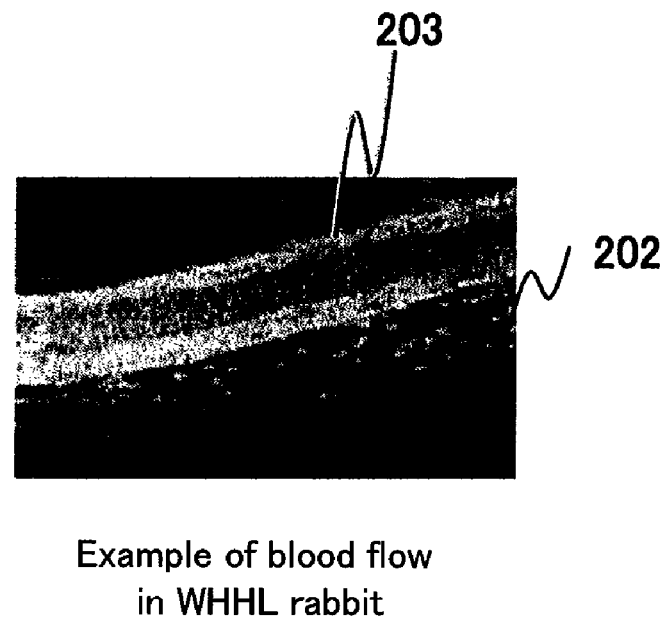
Example of blood flow
in WHHL rabbit

FIG. 16A

|  | During pressure applying (a) | At release (b) | After release (c) (After 10 seconds) |
|---|---|---|---|
| WHHL Rabbit (A) | 45.9 | 46.7 | 45.2 |
| Normal Rabbit (B) | 46.7 | 43.5 | 42.4 |

FIG. 16B

|  | Quadratic differential (Maximum value) |
|---|---|
| WHHL Rabbit (A) | -2.3 |
| Normal Rabbit (B) | 2.1 |

FIG. 16C

|  | Number of leucocytes (/μl) | Number of erythrocytes ×10$^4$ (/μl) | Hematocrit (%) | Tryglyceride (mg/dl) | Total cholesterol (mg/dl) | HDL cholesterol (mg/dl) | LDL cholesterol (mg/dl) |
|---|---|---|---|---|---|---|---|
| WHHL Rabbit (A) | 5600 | 623 | 40.6 | 165 | 537 | 9 | 468 |
| Normal Rabbit (B) | 3400 | 510 | 33.9 | 22 | 96 | 67 | 31 |

BLOOD FLOW MEASURING AND EVALUATING APPARATUS

CLAIM OF PRIORITY

The present application claims priority from Japanese application JP 2007-153491 filed on Jun. 11, 2007, the content of which is hereby incorporated by reference into this application.

BACKGROUND OF THE INVENTION

1. Field of the Invention

The present invention relates to an apparatus for measuring and evaluating blood flow in a superficial blood vessel using high-frequency ultrasound waves.

2. Description of the Related Art

Recently, lifestyle-related diseases including hyperlipidemia, high blood pressure, diabetes, and visceral fat obesity have become issues, and there is an increasing need for early detection or prevention of these lifestyle-related diseases.

There is an ultrasonic B-mode imaging technique for evaluating a degree of blood cell aggregation which is a potential risk factor of incidence or progression of arterial sclerosis, or thrombus formation (for example, see Japanese Patent Application Laid-Open No. 2005-110724). There is also a study on the simulation for frequency dependence of ultrasonic back scattering on a difference in degree of red blood cell aggregation (for example, see David Savery and Guy Cloutier, "A point process approach to assess the frequency dependence of ultrasound back scattering by aggregating red blood cells", J. Acoust. Soc. Am. 110(6), 2001).

In the method disclosed in Japanese Patent Application Laid-Open No. 2005-110724, a dynamic property of the blood cannot be evaluated. Although an apparatus to measure the dynamic property of the red blood cells in vitro exists, its measurement results do not indicate blood flow kinetics in the living body. That is, currently the method for invasively measuring and evaluating the dynamic property of the blood flow in human beings in vivo is not established.

In David Savery and Guy Cloutier, "A point process approach to assess the frequency dependence of ultrasound back scattering by aggregating red blood cells", J. Acoust. Soc. Am. 110(6), 2001, the coagulation time of a pig's blood sample is assumed to represent a red blood cell aggregation rate, and the degree of back scattering in high frequencies of 12.5 MHz or more is estimated by simulation based on experimental data in relatively low frequencies of 3.5 MHz to 12.5 MHz.

Human skin is acoustically different and varies from individual to individual, therefore it is difficult to measure the blood flow in human skin under the same condition without the influence of individual differences.

An object of the invention is to provide means for measuring and evaluating the dynamic property of the blood flow in the superficial blood vessels of human beings in vivo. Another object of the invention is to provide a method for measuring the ultrasound wave under the same condition irrespective of the influence of individual differences.

SUMMARY OF THE INVENTION

In order to solve the problem, the present invention is a blood flow measuring and evaluating system including a signal processing unit for transmitting and receiving an ultrasound to and from the superficial blood vessel of the living body to process the acoustic received signal.

In accordance with an aspect of the invention, an ultrasonic radiation apparatus includes an ultrasonic radiation unit for irradiating a test specimen with an ultrasonic signal; a reception unit for receiving an ultrasound from the test specimen; an image data processing unit for producing plural pieces of image data based on a signal received by the reception unit; a blood vessel signal estimating unit for estimating a range of a location and area of a venous blood vessel and blood flow of the test specimen from the image data; a computing unit for performing Fourier transform to the location and area of a venous blood vessel and blood; and an evaluation unit for evaluating blood state information on the test specimen based on computation result of the computing unit.

In accordance with the present invention, the dynamic property of the blood can be noninvasively evaluated.

BRIEF DESCRIPTION OF THE DRAWINGS

FIG. 2 shows an example of a B-mode image of blood flow in the superficial blood vessel;

FIGS. 16A, 16B and 16C show tables for evaluating a blood property and a table of measured data of blood test.

DESCRIPTION OF REFERENCE NUMERALS

Figure 1A:
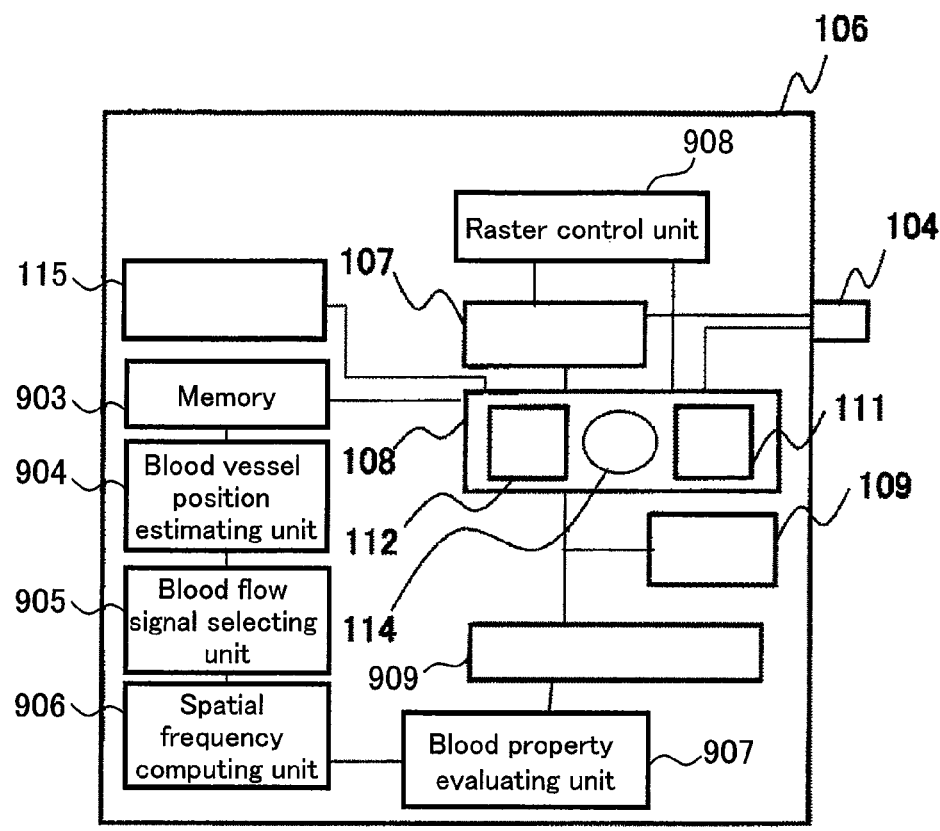
FIGS. 1A and 1B show an ultrasonic data obtaining apparatus aimed at the measurement of a superficial blood vessel in a living body.

101: Human hand
102: Target blood vessel such as superficial blood vessel
103: Transducer
104: Antenna
105: Radio wave
106: Ultrasonic measuring apparatus
107: Control unit for transmitting signal
108: Signal processing unit for processing received wave signal
109: Storage unit
110: Skin
111: Blood property determination unit
112: Image data processing unit 113: Pressure applying unit
114: Time measuring unit
115: Warning unit
201: Example of B-mode image of blood flow in normal individual
202: Example of B-mode image of blood flow in WHHL Rabbit
203: Blood vessel wall
301: Blood flow is stopped by pressing blood vessel
302: Temporal imaging of B-mode still image in a process of releasing press
303: Determination of blood flow area whose data is processed
304: FFT computation processing
305: Computation of integrated signal value
306: Quadratic differential processing
307: Computation of maximum value
308: Display of result
601: Blood flow is stopped by applying pressure on superficial blood vessel
602: Increased blood cell aggregation
603: Pressure on blood vessel is released
604: Decreased blood cell aggregation in a process of restart of the blood flow
605: Stimulus such as lifting of arm is given to blood flow
606: Blood pressure is locally increased by gravity
607: Blood flow velocity is increased
608: Detection of target size being reduced by blood cell aggregation decrease
701: Hair
702: Intercalated portion
800: Start measurement
801: Control pressure-applying method on blood vessel
802: Perform B-mode imaging
803: Estimate blood vessel position
804: Measure reflection intensity
805: Blood vessel position is largely changed?
806: N-time measurements is ended ?
807: Perform noise reduction processing
808: M-time measurements is ended ?
809: End measurement
810: Perform B-mode imaging and select raster
811: Perform A-mode imaging
901: Input unit
902: A/B-mode switching unit
903: Memory
904: Blood vessel position estimating unit
905: Blood flow signal selecting unit
906: Spatial frequency computing unit
907: Blood property estimating unit
908: Raster control unit
909: Display unit
1000: CCD camera
1001: Display image
1002: Camera image
1003: Transducer position display

DESCRIPTION OF THE PREFERRED EMBODIMENTS

Preferred embodiments of the present invention will be described below with reference to the drawings.

First Embodiment

In a first embodiment, a measurement target is a human being. However, the measurement target is not limited to human being, but can also be used on an experimental animal but also measurement and evaluation for a property of a fluid flowing in a relatively superficial part of a certain substance.

Figure 1B:
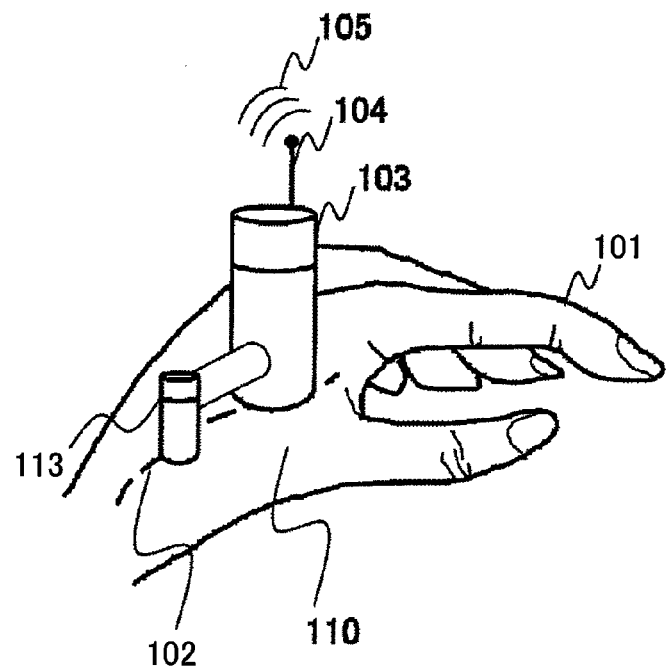

FIGS. 1A and 1B show a configuration of an ultrasonic data obtaining apparatus aimed at measurement of a superficial blood vessel in a living body. FIG. 1A shows the configuration of the apparatus, and FIG. 1B particularly shows a configuration of an ultrasonic transducer. An ultrasonic transducer 103 is put on an individual's skin 110 and an ultrasound is transmitted to a target blood vessel 102 such as the superficial blood vessel of the individual 101 and further receives the signal from it. The ultrasonic transducer 103 receives a control signal for transmitting the ultrasound from an ultrasonic measuring apparatus 106 and sends an acoustic signal received from the measurement object to the apparatus 106 in the form of a wireless signal 105 through an antenna 104. However, the control signal and the acoustic reception signal are not limited to the wireless signal 105, alternatively the ultrasonic transducer 103 and the ultrasonic measuring apparatus 106 may be connected to each other with a cable to transmit and receive the signals.

In addition to a method for fixing the ultrasonic transducer 103 by human hands, movement and positioning of the ultrasonic transducer 103 can be performed by attaching the ultrasonic transducer 103 to a jig such as an xyz stage which enables three-dimensional positioning. In addition to positioning of the ultrasonic transducer 103 to the superficial blood vessel by sight, there is also a method using an optical measurement technique. Hemoglobin in the blood has relatively high near-infrared absorbance in body tissue, and the reflection intensity of visible light (such as green light) is high in a region where the superficial blood vessel exists. Therefore, the ultrasonic transducer 103 can be positioned by detecting the region where the superficial blood vessel exists.

The ultrasonic measuring apparatus 106 includes a control unit 107 used to transmit and receive the ultrasound, a signal processing unit 108 used to process the acoustic signal received from the measurement object, a storage unit 109 in which data is stored, and a display unit 909 used to display measurement results.

The signal processing unit 108 includes a blood property determination unit 111. In the case of a B-mode, the signal processing unit 108 includes an image data processing unit 112.

The display unit 909 displays the received signal and signal processing result in the case where the ultrasonic measuring apparatus is in an A-mode, and the display unit 909 displays an image generated by the image data processing unit 112 in the case where the ultrasonic measuring apparatus is in the B-mode. An electronic scanning method in which a well-known phased array is used may be adopted to take a B-mode image, or a mechanical scanning method in which, with the use of one-channel transducer and the accompanied control circuit and signal processing circuit, the transducer is mechanically scanned with a motor adapted to take a B-mode image. Advantages of the electronic scanning method are that not a continuous raster but a discrete sample volume can be specified in lateral direction and a focal position can be controlled in a depth direction. On the other hand, the mechanical scanning method can realize miniaturization of the apparatus, low power consumption, and low cost.

A specific method for measuring and evaluating the dynamic property of the blood will be described below. With ultrasounds, since the frequency is high, smaller object can be visualized, while a distance in which the ultrasound reaches the inside of the living body becomes shallower. In the ultrasonic frequency with which the living body is radiated, the ultrasounds having high frequencies of about 30 MHz or more are effectively used in measuring the blood flow of superficial blood vessel.

FIG. 2 shows an example of the B-mode image of the blood flow in the actual superficial blood vessel. In this example, a rabbit is the measurement target. FIG. 2 shows an example 201 of a blood flow image in a normal individual and an example 202 of a blood flow image in a WHHL Rabbit (Watanabe heritable hyperlipidemic rabbit). The WHHL Rabbit has a genetic deficiency of a LDL (low-density lipoprotein) receptor, hypercholesterolemia appears from birth in the WHHL Rabbit, and serum triglyceride levels of the WHHL Rabbit are over ten times higher than that of normal individuals. In FIG. 2, a blood vessel wall 203 is observed as a layer having higher brightness values in the image. The high-brightness portion in the blood mainly represents the presence of the red blood cells. It is found that the blood is observed to have higher brightness in the individual that have hypercholesterolemia which causes red blood cell aggregation, as compared to normal individuals. The samples of blood having different properties are dynamically measured and evaluated by the following procedure.

Figure 3:
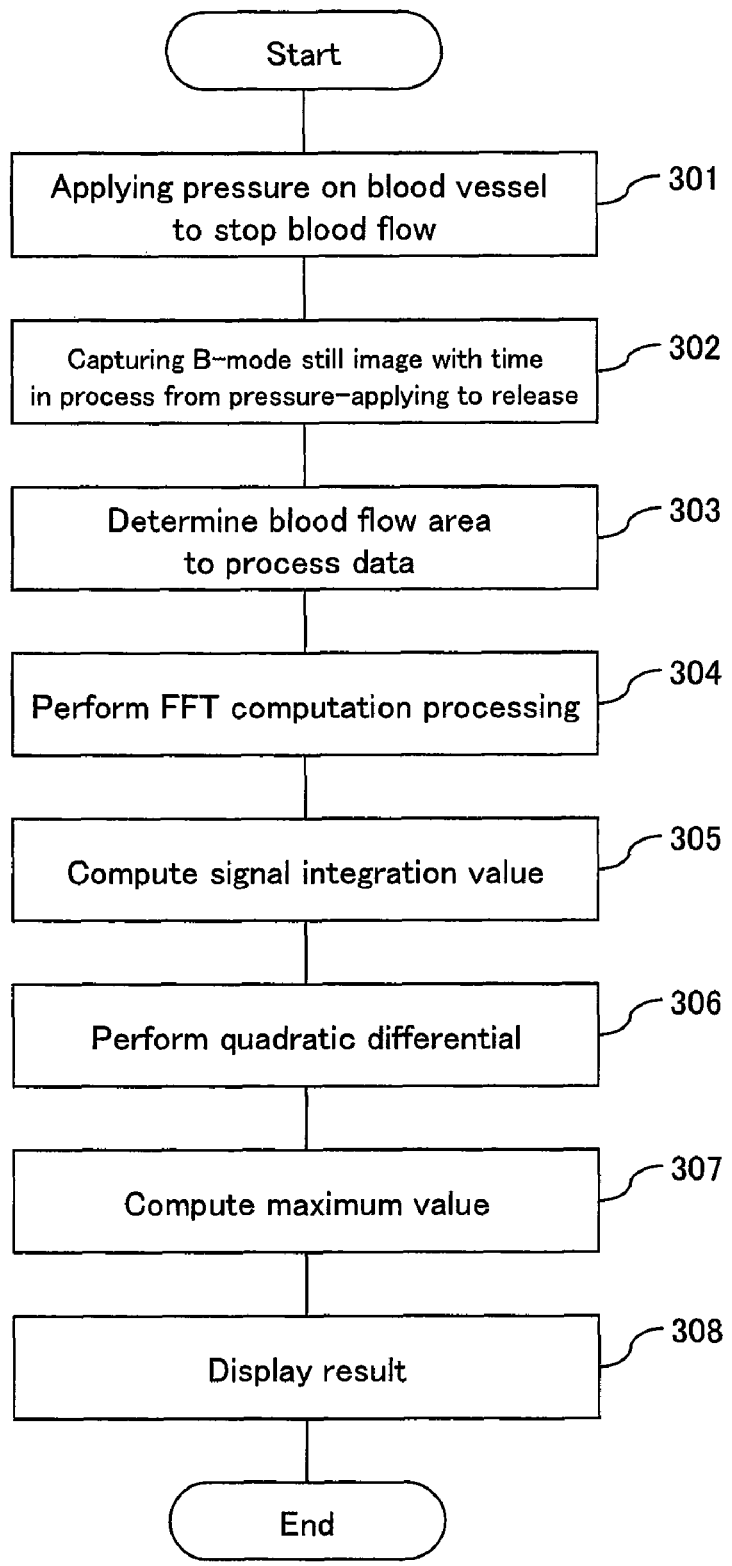
FIG. 3 is a flowchart showing a sequence for measuring a blood state.

FIG. 3 is a flowchart showing a sequence for dynamically measuring and evaluating the blood property. The blood flow is temporarily stopped by applying a physical stimulus such as pressure on the superficial blood vessel (S301). The manipulation is effectively performed using a pressure applying unit 113 which stimulates a position far away from a blood flow observation region used by the ultrasonic transducer 103. Although an avascularization band may be used in blood collection, FIG. 1 shows the ultrasonic transducer 103 including the pressure applying unit 113. The pressure applying unit 113 is attached not to the ultrasonic transducer 103 but to the ultrasonic measuring apparatus 106, and the first embodiment is not limited to the configuration shown in FIG. 1.

Applying pressure on the superficial blood vessel is not performed for more than one minute, because in some cases prolonged avascularization causes formation of hematomas. Therefore, the apparatus includes a time measuring unit 114 such as a timer which is effectively formed such that a warning unit 115 provides a warning after one minute to release the applied pressure. The time measuring unit 114 is provided on the side of the ultrasonic measuring apparatus 106, and only a command signal for releasing the pressed blood vessel is effectively transmitted through a cable or a wireless signal 105 to manipulate the pressure applying unit 113. Alternatively, the time measuring unit 114 may be provided on the side of the ultrasonic transducer 103 or pressure applying unit 113. From the start of applying pressure on the blood vessel to the pressure release, plural images are captured with time (S302). For example, the images in the following three states are obtained: (a) The state in which pressure is applied on the blood vessel to stop the blood flow; (b) The state in which the blood begins to flow when the pressure is released; (c) The state in which a predetermined time has elapsed after the pressure is released.

A blood flow area (rectangular or raster) to process is determined in the captured image using the blood vessel position estimating unit and the blood flow signal selecting unit (S303). The processing is performed as follows. An arbitrary size rectangular area (or raster) is determined by checking visually the B-mode image. In this case, it is effective that software of the apparatus has this function. Then, the position where the pixel values are changed in the image is detected by differential processing, because the pixel values are largely changed at a boundary between the blood vessel and the blood (blood vessel portion has the high intensity pixel values and the blood has the low intensity values). This process enables the blood vessel position to be identified and the rectangular area (or raster) for data processing to be selected inside the blood vessel.

Figure 4:
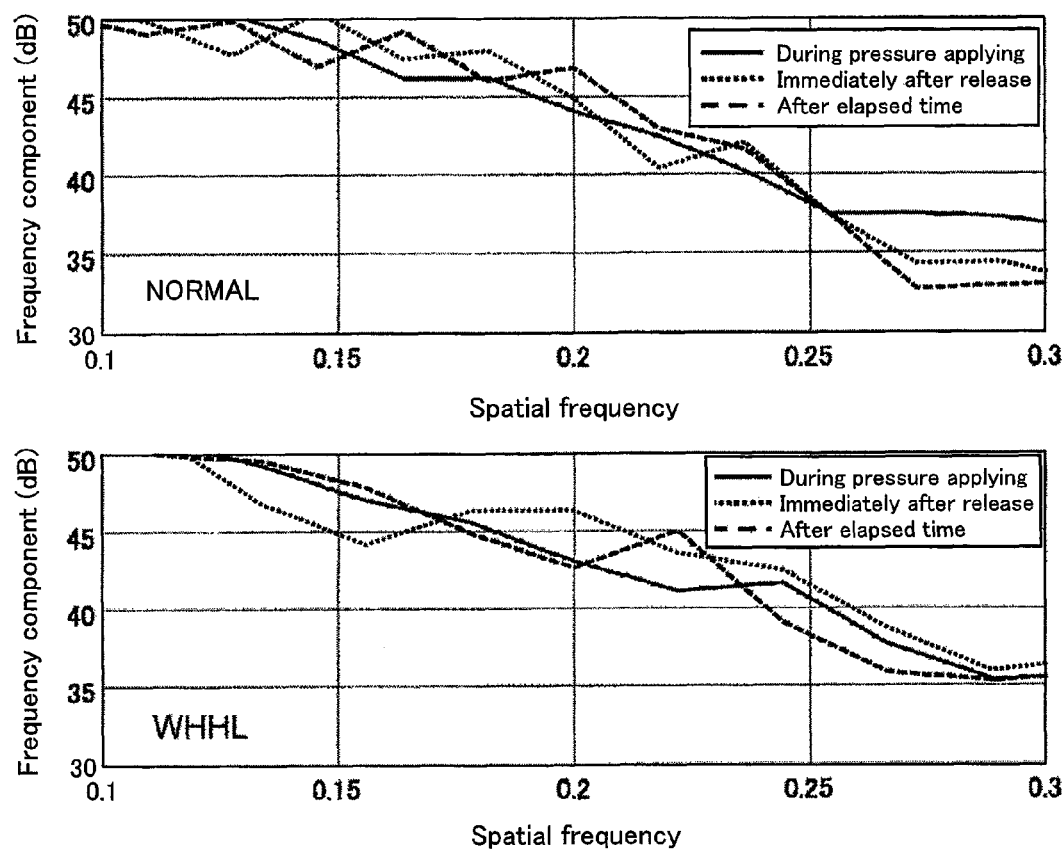
FIG. 4 shows an exemplary result of FFT computation processing of the B-mode image in stimulus response.

The spatial frequency computing unit performs FFT processing in the selected area (S304). The FFT processing may be performed two-dimensionally or one-dimensionally. FIG. 4 shows an example of the one-dimensional processing result. As can be seen from the result of FIG. 4, a difference in blood between the Normal Rabbit and the WHHL Rabbit can be detected by a time course of a component near a spatial frequency of 0.3/pixel. A wavelength corresponding to about three pixels is a detection limit size of a blood speckle as the current measurement target, and the blood property can dynamically be evaluated by observing a variation of the component. In the current measurement, because one pixel corresponds to 20 micrometers, the three pixels are equal to 60 micrometers, namely the aggregation size is about eight times the diameter of the largest blood cells is observed.

The speckle size is a result of two-dimensional convolution between a spatial distribution of measurement objects and a point response function of the measuring system. In the case where a shape of the point response function of the measuring system is not changed, the spatial distribution of objects represents the speckle size. In the WHHL Rabbit, the blood flow is not largely changed by the pressure and release because blood cells aggregation increases basically. On the other hand, in the Normal Rabbit, the aggregation does not increase basically. However, the aggregation increases when the blood flow is interrupted by applying pressure on blood vessels, and the aggregation disappears when the blood flows again after releasing the pressure. In the measuring system, it is estimated that the size of the aggregated blood-cell cluster is substantially equal to a magnitude of the point response function, so that the change caused by the aggregation appears most remarkably at the limit of the speckle size.

Figure 15:
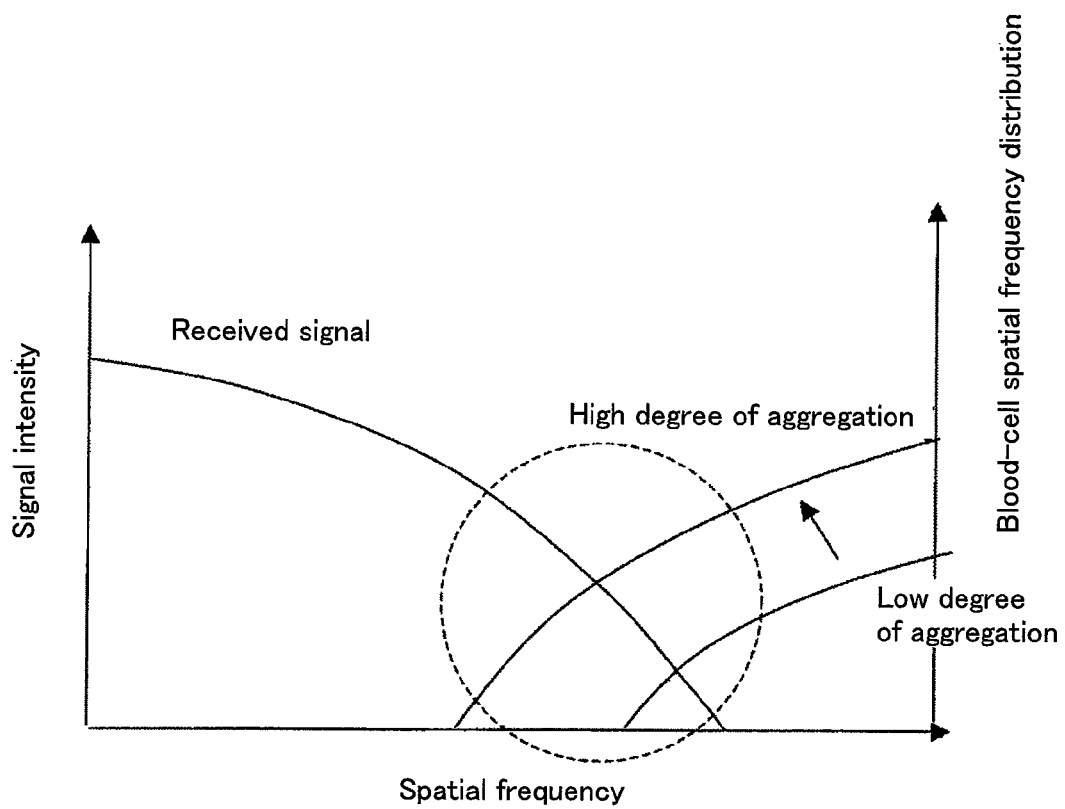
FIG. 15 shows a schematic view of a blood-cell spatial frequency distribution.

FIG. 15 is a schematic view explaining the aggregation of the blood cells. A horizontal axis represents the spatial frequency. When the aggregation of the blood cells increases, the spatial frequency distribution of the blood cells is shifted toward the low-frequency side (arrow in FIG. 15). When a skirt portion of a sensitivity distribution of the received signal exists in an area surrounded by a dotted line, the change of aggregation can be analyzed with high sensitivity by processing the signals in the area surrounded by the dotted line.

Therefore, the degree of blood cell aggregation can be investigated by focusing on the signal of the skirt portion of the spatial frequency distribution of the signal shown in FIG. 4. Obviously, the ultrasound frequency is increased to decrease the speckle size, and the sensitivity to a change in aggregation can be increased. However, attenuation of the ultrasound increases such that the ultrasound signal is hardly received. From the standpoints of the ultrasonic attenuation and sensitivity to the change of aggregation, it is necessary that the optimum frequency be selected according to a distance from a body surface to the blood vessel.

As used herein, the spatial frequency shall refer to the fineness of a periodic structure constituting the image. The spatial frequency is represented by the number of periods having sine intensity distributions in unit length. The Fourier transform is performed to the image to break down the image into the spatial frequency components, which enables the image to be evaluated. The upper limit of the spatial frequency which becomes the measurement target is set not lower than the blood cell size, and desirably the upper limit of the spatial frequency is set to about $\frac{1}{8}$ ($\mu m^{-1}$) of an inverse number of the blood cells. Although the rabbit used in the current experiment has a congenital disease, practically it is necessary to detect the change in blood property before the disease has developed. Therefore, the spatial frequencies higher than 1/60 ($\mu m^{-1}$) which is of the experimental detection limit shown in FIG. 4 is required for the lower limit of the spatial frequency. Thus, from the standpoint of the spatial frequency, desirably the apparatus has the measurement range of 1/60 to 1/8 ($\mu m^{-1}$). On the other hand, the spatial frequency in a depth direction and the spatial frequency in a lateral direction are discussed as follows. First, as to the depth direction, in the ultrasonic imaging, an envelope of the received signal is detected in order to ensure a wide dynamic range, and logarithm compression is performed to the envelope of the received signal to produce the image. The spatial frequency is determined by multiplying a center frequency of the actual acoustic transmission wave by the number of cycles of the acoustic transmission wave in order to detect the envelope of the received signal. Second, as to the lateral direction, a beam width determining the spatial frequency can be obtained by the following equation. Because directionality of a rectangular transducer is expressed by $\sin(ka \cdot \sin \theta)/(ka \cdot \sin \theta)$, $\sin(ka \cdot \sin \theta)/(ka \cdot \sin \theta)=0.5$ is substantially obtained in the case of $ka \cdot \sin \theta = 1.9$. Where k is a wave number, 2a is a bore diameter, and θ is a directivity angle. Assuming that L is a beam width, F is a focal distance, f is an ultrasonic frequency, and v is an acoustic velocity in the living body, L satisfying Formula 1 is expressed as follows.

$$\frac{2\pi fa}{v} \sin\left(\tan^{-1} \frac{L}{2F}\right) = 1.9 \quad \text{[Formula 1]}$$

That is, Formula 2 can be obtained.

$$L = 2F \tan\left(\sin^{-1}\left(\frac{v}{\pi fa}\right)\right) \quad \text{[Formula 2]}$$

The information on the blood cell property is obtained by determining the focal distance F, the ultrasonic frequency f, and the bore diameter width a, and the apparatus can be configured so as to suitably estimate the blood cell property.

Figure 5:
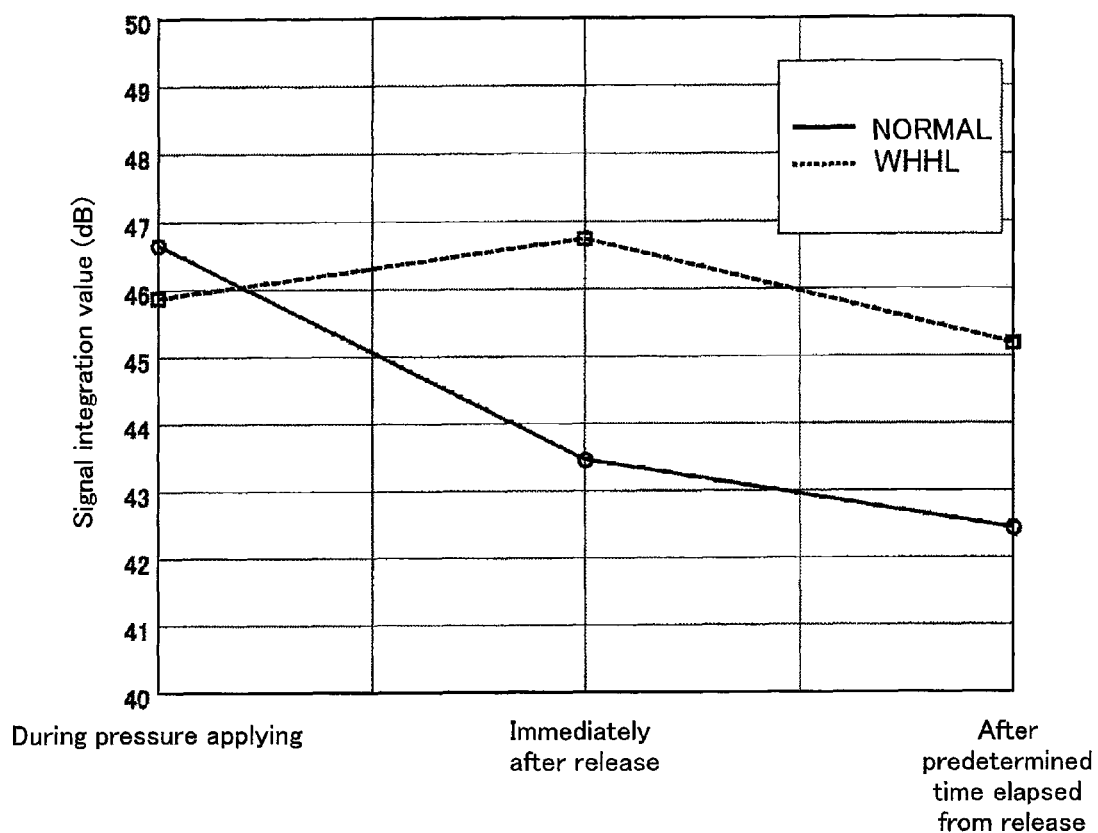
FIG. 5 shows an example of a change in evaluating ultrasonic signal intensity in the stimulus response.

The state of FIG. 4 is evaluated by the following method. An integration value is computed for the signal near the spatial frequency of 0.3 (in this case, 0.275 to 0.3) (S305). The integration value is computed in each of the states (a), (b), and (c) for 302. FIG. 5 and Table of FIG. 16A show result examples. The WHHL Rabbit has the small change in signal intensity compared with the Normal Rabbit. The blood property is evaluated based on the change in signal intensity.

In evaluating the blood property, the pieces of information on the blood cell property and blood property are obtained from the information on the blood cell property obtained by the FFT computation processing. That is, the information on the blood cell property and the corresponding pieces of information on the blood cell property and blood property are read from a blood cell property and blood property information table stored in the blood property estimating unit.

The following processing is performed to evaluate the state of the change with time. Quadratic differential filtering processing of a=[1-2 1] is performed to a one-dimensional array (in this case, numerical values of (a), (b), and (c) in Table 1A) of the change with time of the computed integration value (S306), and the maximum absolute value of the result is determined (S307). It is assumed that a SS value is the maximum absolute value. Table of FIG. 16B shows an example of the result. A property of the blood flow in the living body can be evaluated by the comparison of the values in Table 1B, and the all the conditions such as the aggregation state of the blood cell and viscosity represent the property of the blood flow. For example, when a threshold is set to zero, the state of the blood flow can be evaluated such that probably the blood is not healthy. In addition, there is a method for evaluating mean gradient. Table of FIG. 16C shows a reference data of the result of the blood test for the WHHL Rabbit and Normal Rabbit used in the experiment. In the WHHL Rabbit, the total cholesterol is exhibited at about ten times the level of a Normal Rabbit. In the lipid-rich blood, because the blood cells are easily aggregated, the sluggish response to pressure release, is observed and therefore the SS value is zero or lower.

The evaluation result of the blood flow obtained based on the measurement result is displayed on the data display unit 909 of the ultrasonic measuring apparatus (S308), and the evaluation result is stored in the storage unit 109 if needed.

The method for performing the evaluation with three points of data obtained with time is described by way of example. However, the time scale used is not limited to the range of the three points, but a longer time course from the pressure release to the steady state may be measured to perform the evaluation.

Figure 6A:
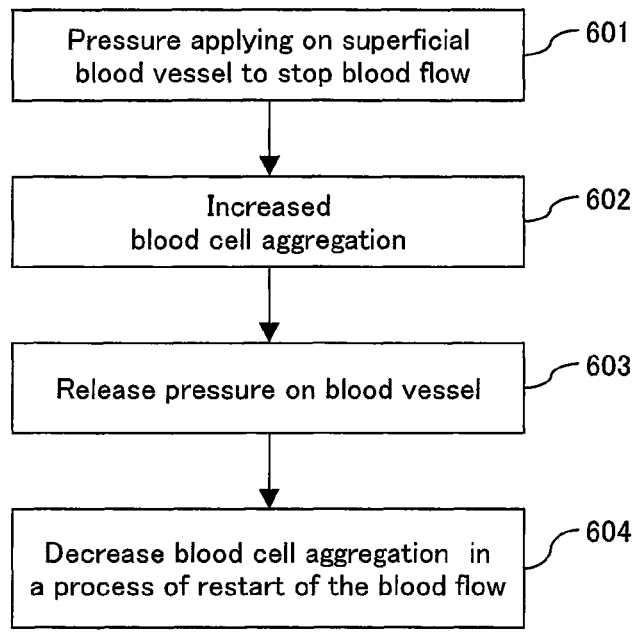
FIGS. 6A and 6B show examples of stimulus given to evaluate the blood state.
Figure 6B:
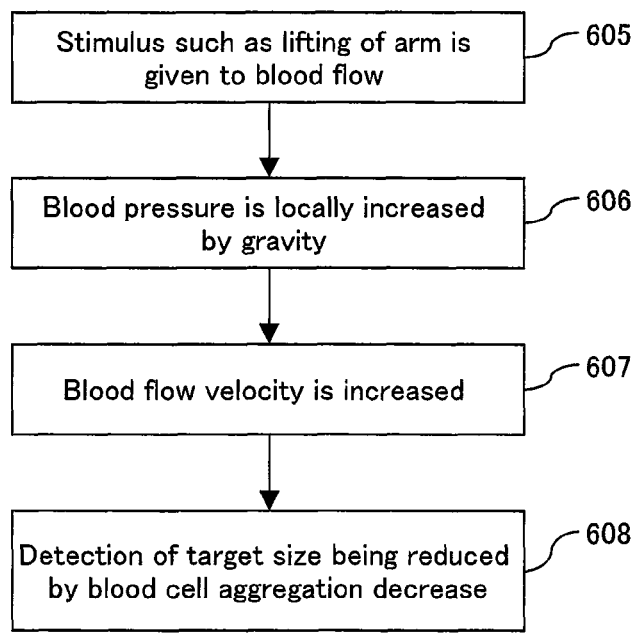

In the above-described method, the pressure is used as the physical stimulus related to the blood flow velocity such that the degree of blood cell aggregation is increased as shown in FIG. 6A. The blood flow is stopped by applying pressure to the superficial blood vessel using the pressure applying unit 113 (S601). That is, the degree of blood cell aggregation is increased (S602). Then, the pressure on the blood vessel is released (S603), and the increased blood cell aggregation begins to be decreased in the process of restart of the blood flow (S604). A method for measuring and evaluating the blood flow in the middle of the transient response is shown. Applying the pressure to the blood vessel, it is necessary that the region of pressure application is located away from the blood flow measurement region to some degeree. That is, it is necessary that the pressure applying unit 113 and the ultrasonic transducer 103 be separated by a predetermined distance. When the blood vessel position in the measurement region is moved to a certain extent, the measured section is shifted, which which can cause disadvantages. On the other hand, as shown in FIG. 6B, the stimulus can be applied such that blood cell aggregation is decreased. When the stimulus such as the lifting of an arm is applied (S605), the blood pressure is locally increased by gravity (S606). In the case where the blood has small viscous resistance to the blood cells (so-called "runny blood"), the blood flow velocity is largely changed when the hand is raised. On the other hand, in the case where the blood has a large viscous resistance to the blood cells (so-called "sticky blood"), the blood flow velocity is not changed as much. The difference in the change can similarly be evaluated by the above-described method.

Figure 7:
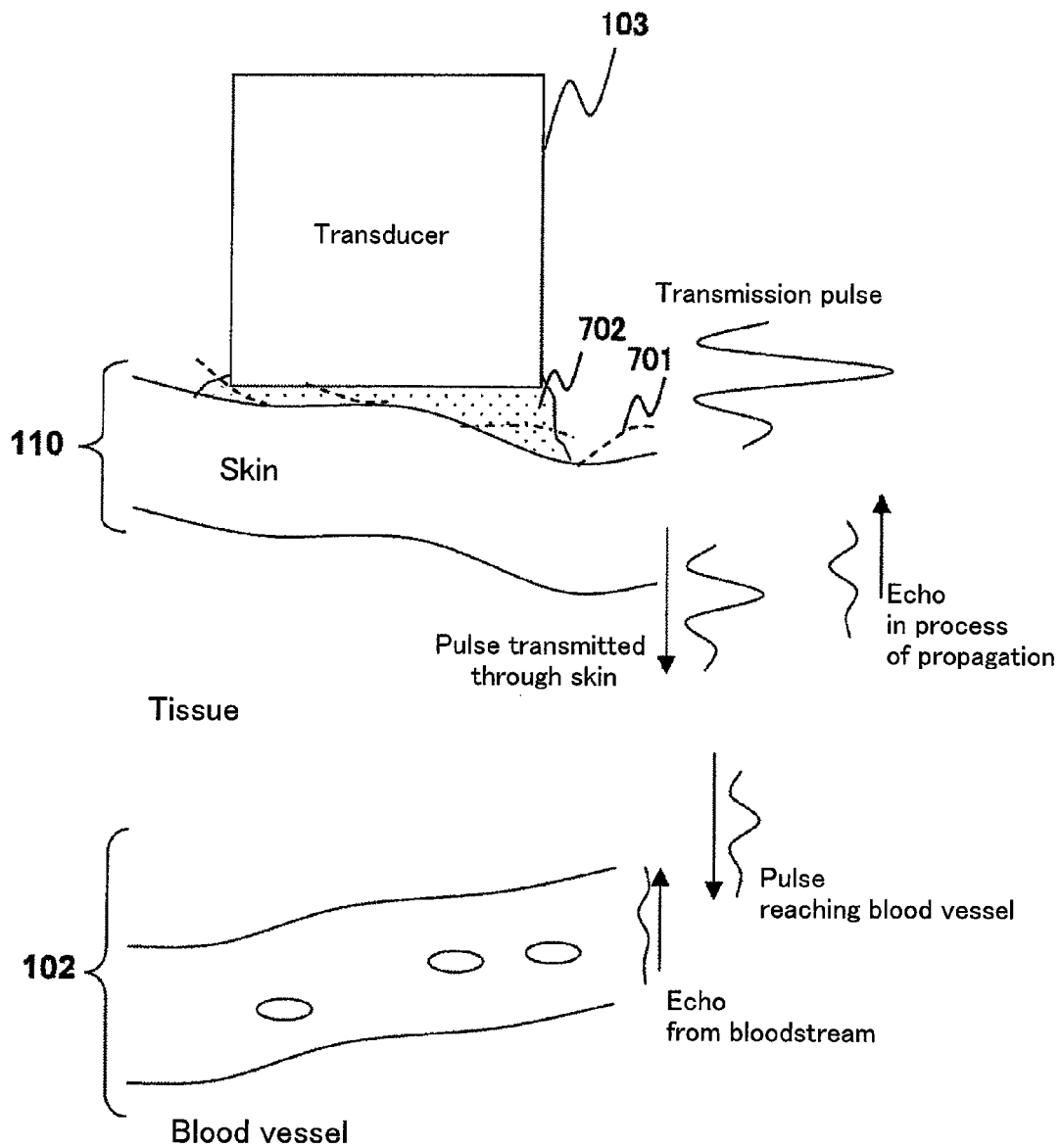
FIG. 7 shows a method for reducing measurement variations according to individual differences or a measurement region and a measurement condition of the same subject.

The case in which measurement variations caused by the individual differences or the measurement region and measurement condition even in the same subject are decreased will be described below with reference to FIG. 7. When the signal is measured from the blood vessel in the living body by the ultrasonic echo method, the state of propagation path has a large influence on the signal intensity or frequency characteristics. A pulse transmitted from the ultrasonic transducer 103 enters the living body through the intercalated portion 702 between the transducer and surface of the body. The pulse propagates while being attenuated and scattered in the skin 110 and the living body tissues located between the skin 110 and the target blood vessel 102, and the pulse reaches the blood vessel 102. As used herein, the intercalated portion 702 shall refer to an acoustic propagation path which is formed by an ultrasound gel between the skin 110 and the ultrasonic transducer 103, and the intercalated portion 702 includes a hair 701 on the body surface. The echo signal reflected from the blood cells in the blood vessel reaches the transducer through the reverse path, and the echo signal is converted into an electrical signal. The acoustic characteristics of the blood vessel wall heavily depends on individual differences in the acoustical path through superficial intercalated portion 702, the skin 110, and the living body tissue between the skin and the target blood vessel 102. Even in the same person, the surface state of the skin depends on the measurement conditions, and usually the same surface state is not maintained. Therefore, the propagation path has a strong influence on the intensity and frequency characteristics of the echo signal derived from the blood cells. It is difficult to remove the influence of the propagation path to obtain only the signal derived from the blood cell property in one-time measurement. Therefore, the blood flow velocity is controlled by applying the pressure on blood vessel or changing the blood pressure, and only the signal component derived from the blood cell property is changed to perform the measurement. This enables the signal derived from the blood cell property to be separated from the influence of the propagation path.

Figure 8:
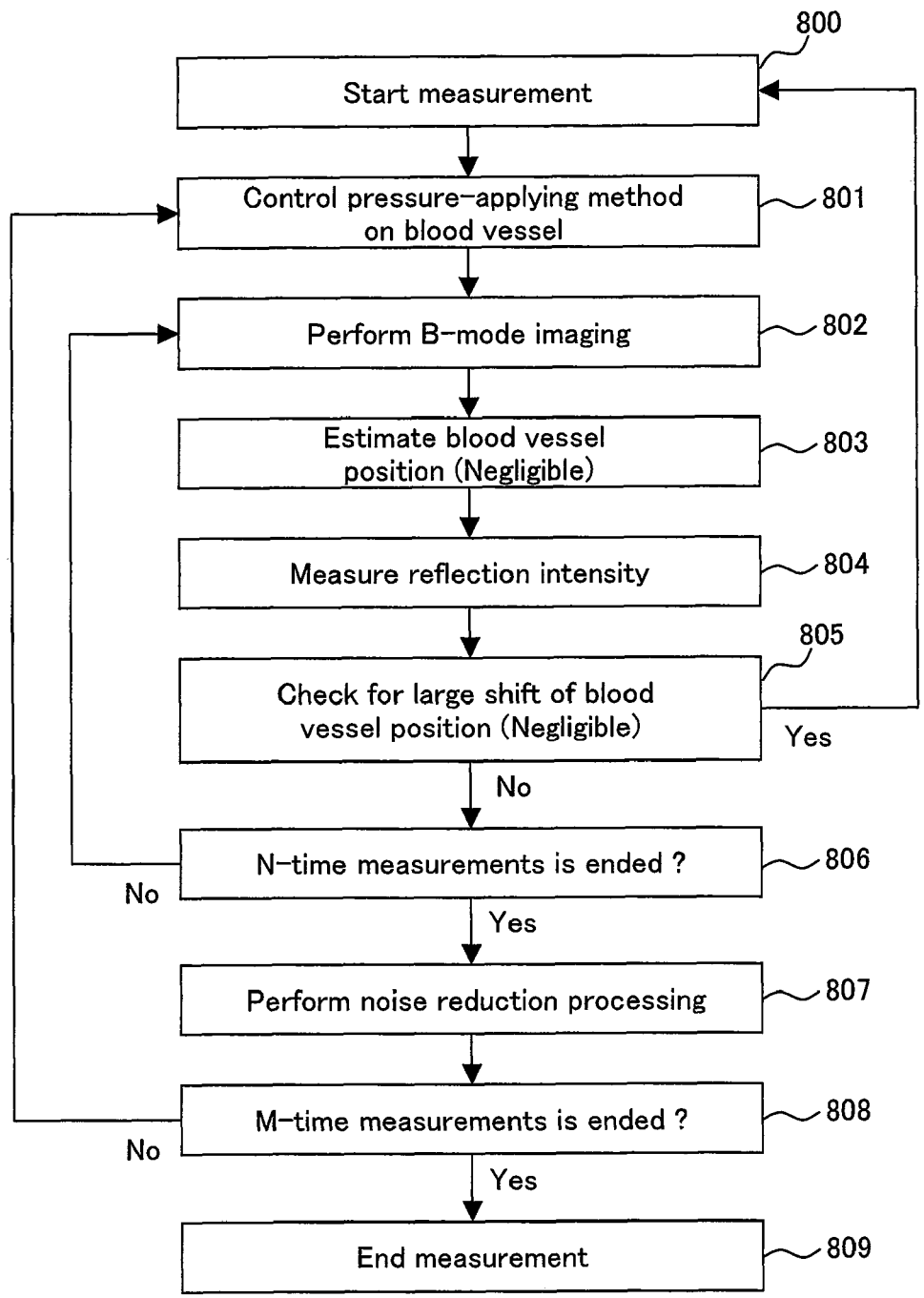
FIG. 8 shows a flowchart depicting a noise reducing method.

A noise reduction method will be described with reference to FIG. 10. There are two factors which cause the noise or measurement variations. First, when the echo signals from tissues except for the blood cells are mixed, relative sensitivity of the measurement is lowered to the change in blood flow property. Second, in the case where an artery is used as the target blood vessel, density of the blood cells per unit volume fluctuates by pulsation of the artery, which causes the measurement variations. The noise reduction method will be described below with reference to a flowchart of FIG. 10. After the measurement start (S800), the blood vessel pressing method is controlled (S801). In this case, pressure-applying method on the blood vessel pressing is controlled using the pressure applying unit 113. Alternatively, the control may be performed using a device such as a cuff. Alternatively, pressure is applied on the blood vessel temporally to interrupt the blood flow, and the elapsed time since the blood flow restarts again may be used as a parameter. Then, the capturing of the B-mode image is performed (S802), and the blood vessel position is estimated by binarization or a region growing in which an area having an arbitrary shape is extracted (S803). The reflection intensity is measured (S804). The reflection intensity is measured N times, and the data is obtained for an interval not lower than one heart beat. The influence of the measurement variations by the pulsation is decreased by averaging. In N-time measurements, when the blood vessel position is periodically estimated (S803), whether or not the measurement region is largely shifted can be checked by checking the large position shift of the blood vessel position (S805). When the measurement region is largely shifted, the blood vessel position is corrected to take the data or the measurement is started again from the beginning. After the N-time measurements are performed (S806), the averaging processing of N times or only the fluctuation component is extracted. This enables the noise to be reduced (S807). The sensitivity for the signal component reflected by the blood property can be improved by extracting only the fluctuation component. The extraction of the fluctuation component is performed by removing the DC component in the frequency space, or by removing the trend on the temporal axis. The measurement processing is repeated while pressure-applying method on the blood vessel is changed. After the measurement shown in FIG. 8 or 9 is completed, the blood property can be measured by the ultrasonic echo method.

Second Embodiment

Figure 12:
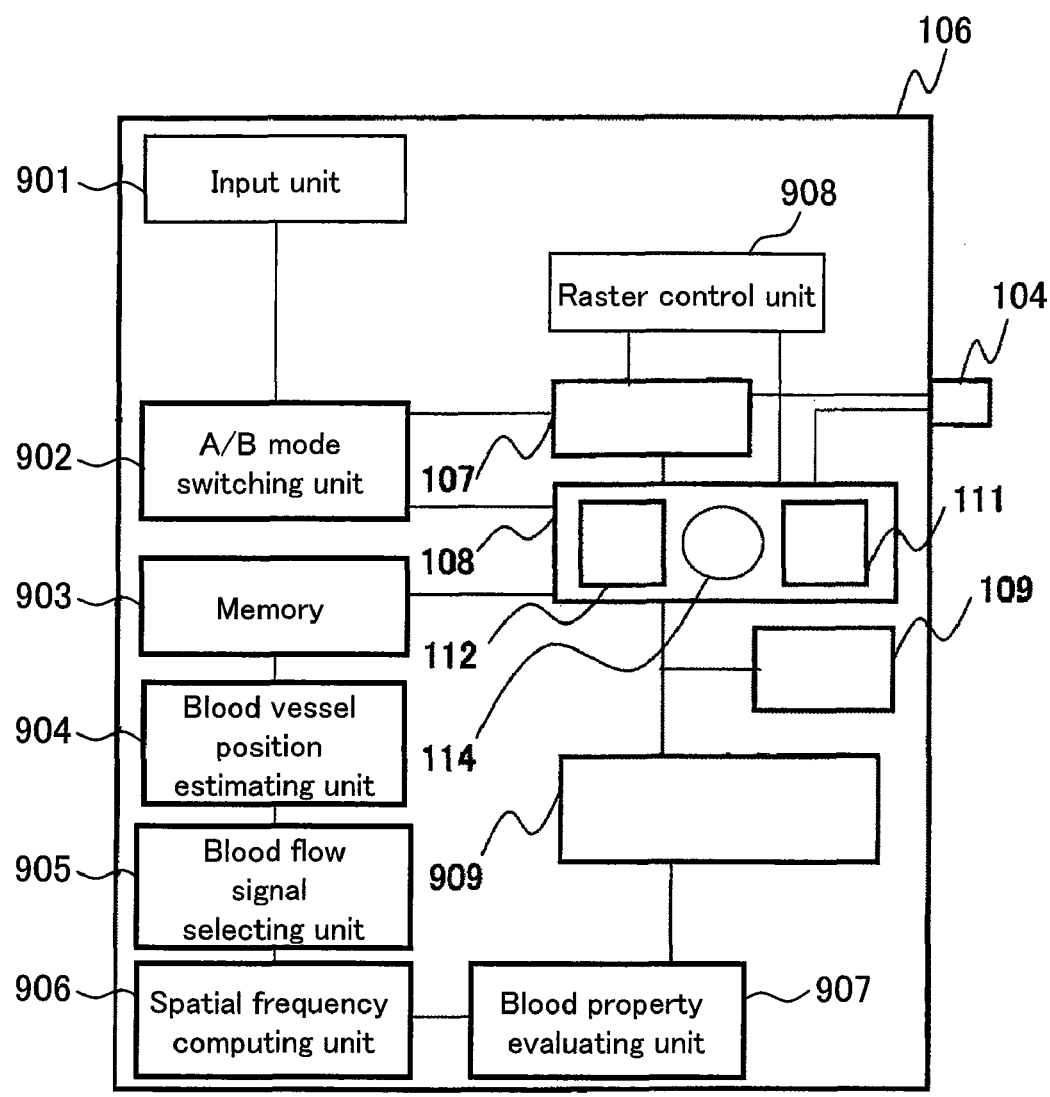
FIG. 12 shows an example of an apparatus configuration.

In a second embodiment, an operator specifies the A-mode measurement position from the B-mode image, and the operator performs the measurement of the reflection intensity. The point of difference from the first embodiment will mainly be described below. Other configurations except for the point described below are basically similar to those of the first embodiment. FIG. 12 shows a configuration of an apparatus of the second embodiment. In the second embodiment, an A/B-mode switching unit 902 can switch between the A-mode and the B-mode in response to an input from an input unit 901. When the raster is fixed by the A-mode switching, the acoustic received wave data of the acoustic received wave processing unit 108 is recorded in the memory 903. In the apparatus configuration of the second embodiment, the data is displayed on the display unit 909 as the computation result concerning the blood property through the blood vessel position estimating unit 904, blood flow signal selecting unit 905, spatial frequency computing unit 906, and blood property estimating unit 907.

Figure 9:
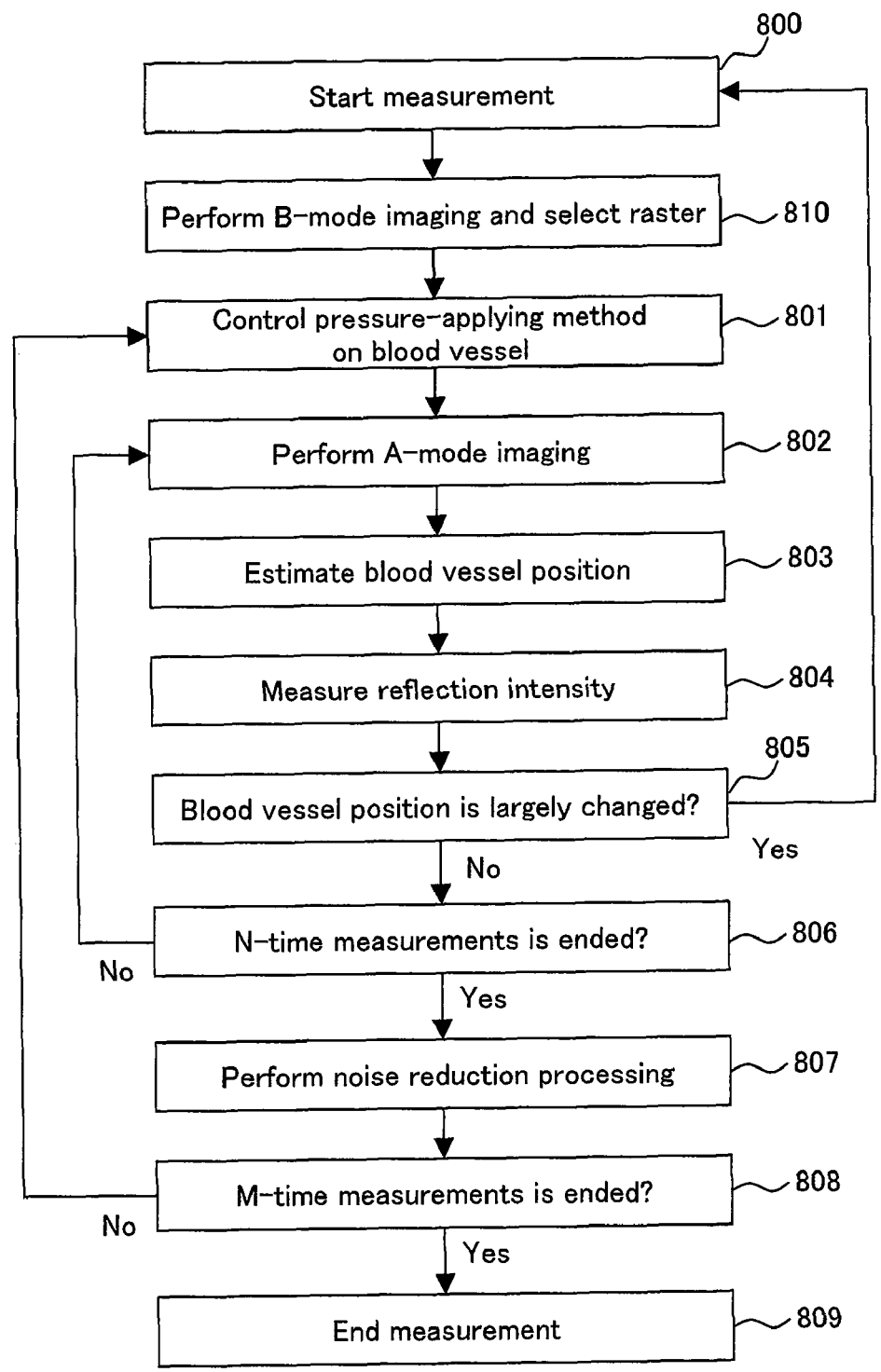
FIG. 9 is a flowchart showing a method for measuring reflection intensity by specifying an A-mode measurement position in the B-mode image.
Figure 10:
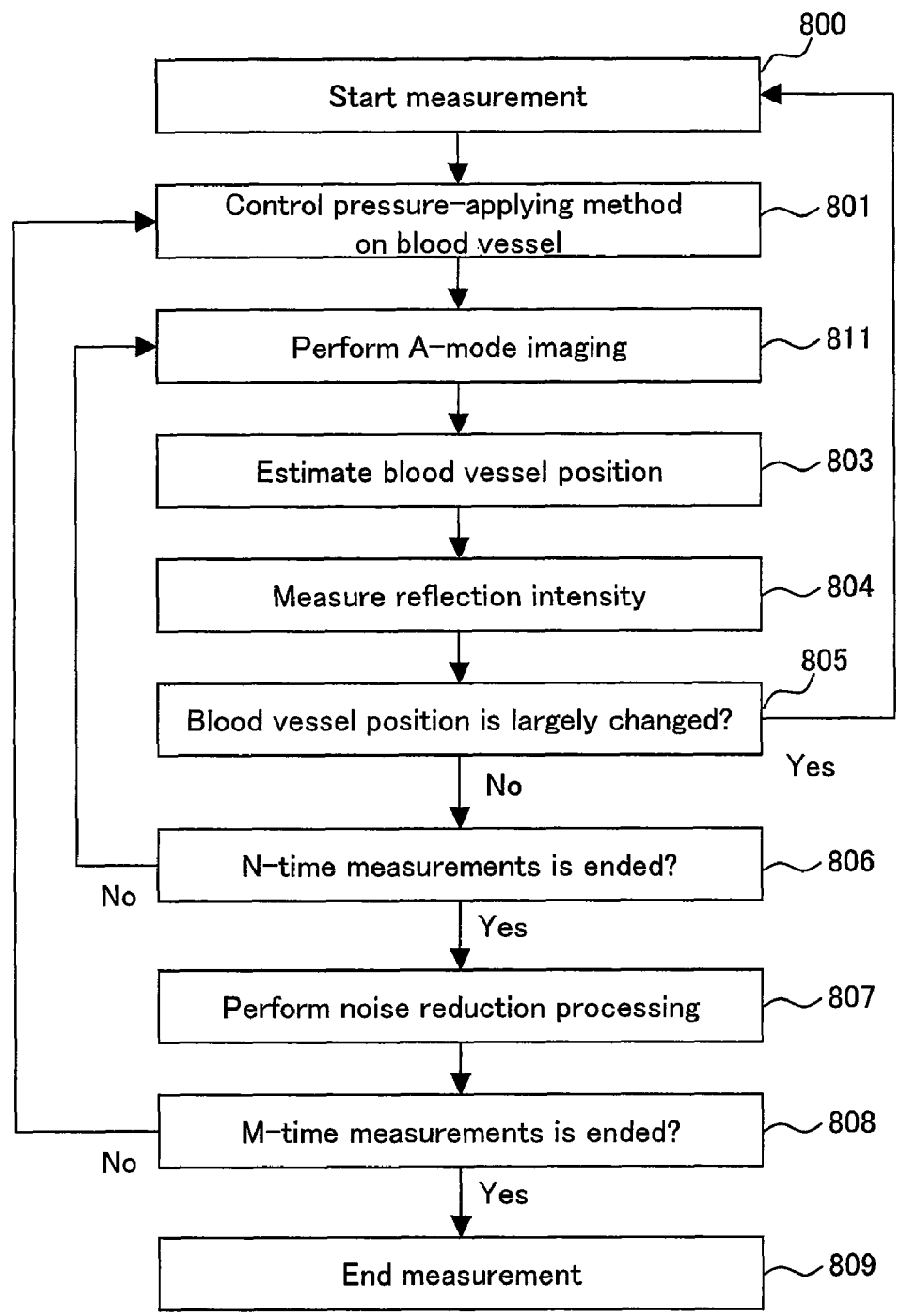
FIG. 10 is a flowchart for measuring and evaluating a degree of blood cell aggregation in the A-mode.
Figure 11:
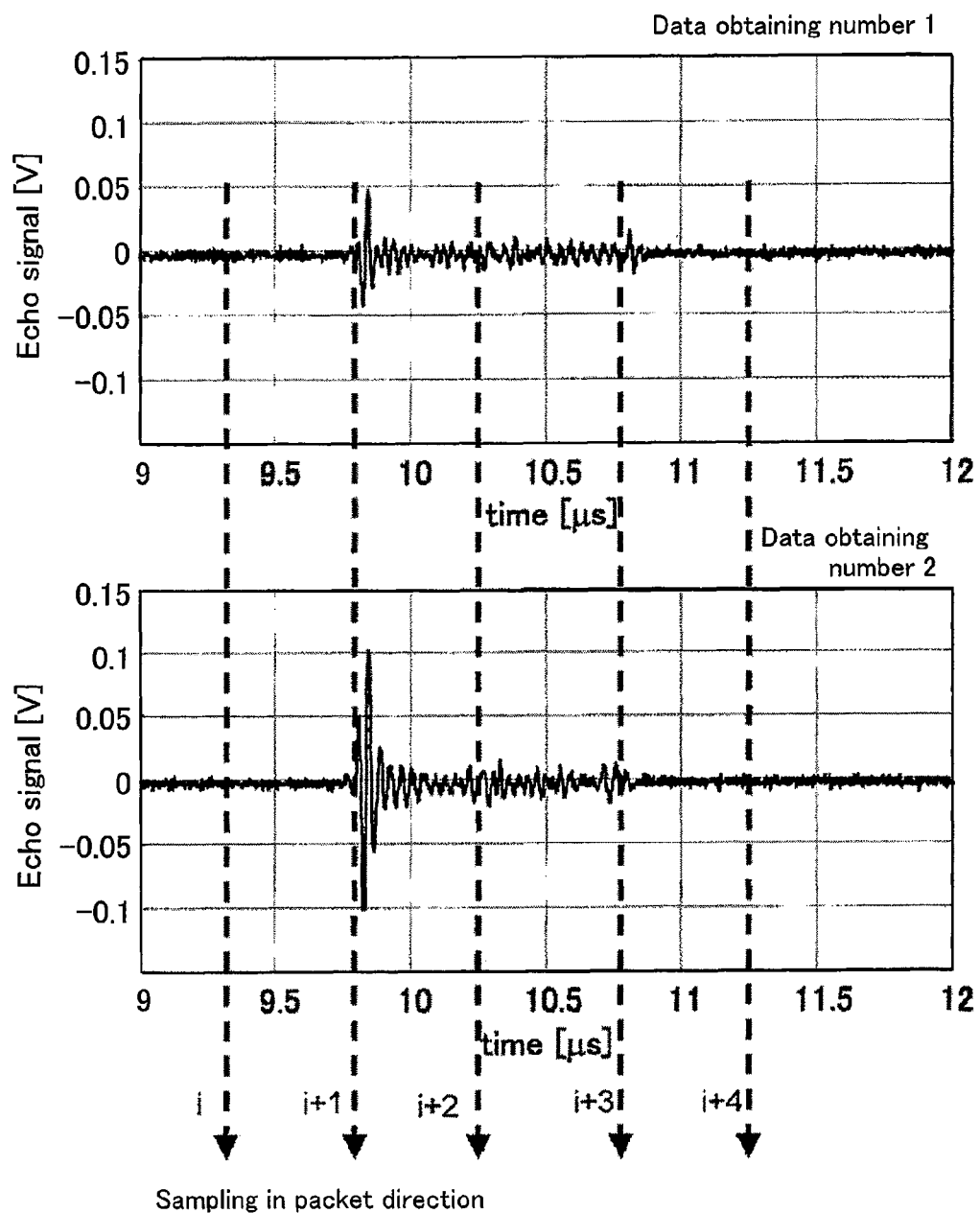
FIG. 11 shows measured data of a reflection echo from an auricle of a rabbit in the A-mode.

FIG. 9 is a processing flowchart of the second embodiment. The operator selects the raster at the same time as the B-mode imaging (S810). Because the A-mode imaging is performed with the raster, so that a data sampling interval can be improved by 10 to 100 times, and the various fluctuation-component extracting methods described in the first embodiment can be adopted. That is, because the B-mode imaging is a technique of repeating the A-mode imaging by the number of raster lines while the raster is moved, the data sampling interval (not the sampling interval of A/D conversion, but time interval during which data is obtained from a certain sample volume) is decreased by the number of raster lines when focusing attention to one raster. However, in the A-mode imaging, it is necessary that the blood vessel position be correctly estimated to confirm whether or not the echo is precisely obtained from reflection and scattering body in the blood vessel. Therefore, the B-mode imaging is periodically performed and the operator visually confirms that the echo is precisely obtained from reflection and scattering body in the blood vessel. Alternatively, the fluctuation is checked during the sampling time. FIG. 11 shows a reflection echo from an ear of the rabbit in the form of RF data in the A-mode. Hereinafter, a continuous set of A-modes is referred to as a packet. The pieces of data at the same sampling point in the packet are arranged, and the pieces of data is divided into the temporally changed sampling point and the temporally unchanged sampling point, which allows the position of the blood vessel to be estimated. Assuming that $a_{i,N}$ is A-mode data at a data obtaining number N and a sampling point i, an A-mode data row is expressed by $A=(a_{1,N}, a_{2,N}, \ldots, \text{and } a_{i,N})$. A data set $Bi=(a_{i,1}, a_{i,2}, \ldots, a_{i,N})$ in which data is reorganized in each data obtaining number in the packet is produced from the A-mode data row to check the change in data in a data obtaining number direction (N direction). Because the signal from the tissue has the small temporal change while the data from the blood vessel has the large temporal fluctuation component, the inside of the blood vessel can be distinguished from the outside based on whether or not the temporal change is larger than a predetermined threshold, which allows the blood vessel position to be estimated. In the single data, it is difficult to distinguish the inside of the blood vessel from the outside. However, the inside of the blood vessel can be distinguished from the outside by the method of the second embodiment. Alternatively, the inside of the blood vessel is effectively distinguished from the outside by well-known techniques such as a power Doppler method. Thus, the combination of the blood vessel position estimating method and the A-mode measurement can improve a frame rate to sensitively measure the blood property. Body motion and the movement of the transducer other than movement of blood become also troublesome. The signal correlation is obtained in the whole of the depth direction to remove the influence of the motion of the whole image, whereby the measurement accuracy is effectively improved.

Third Embodiment

Figure 13:
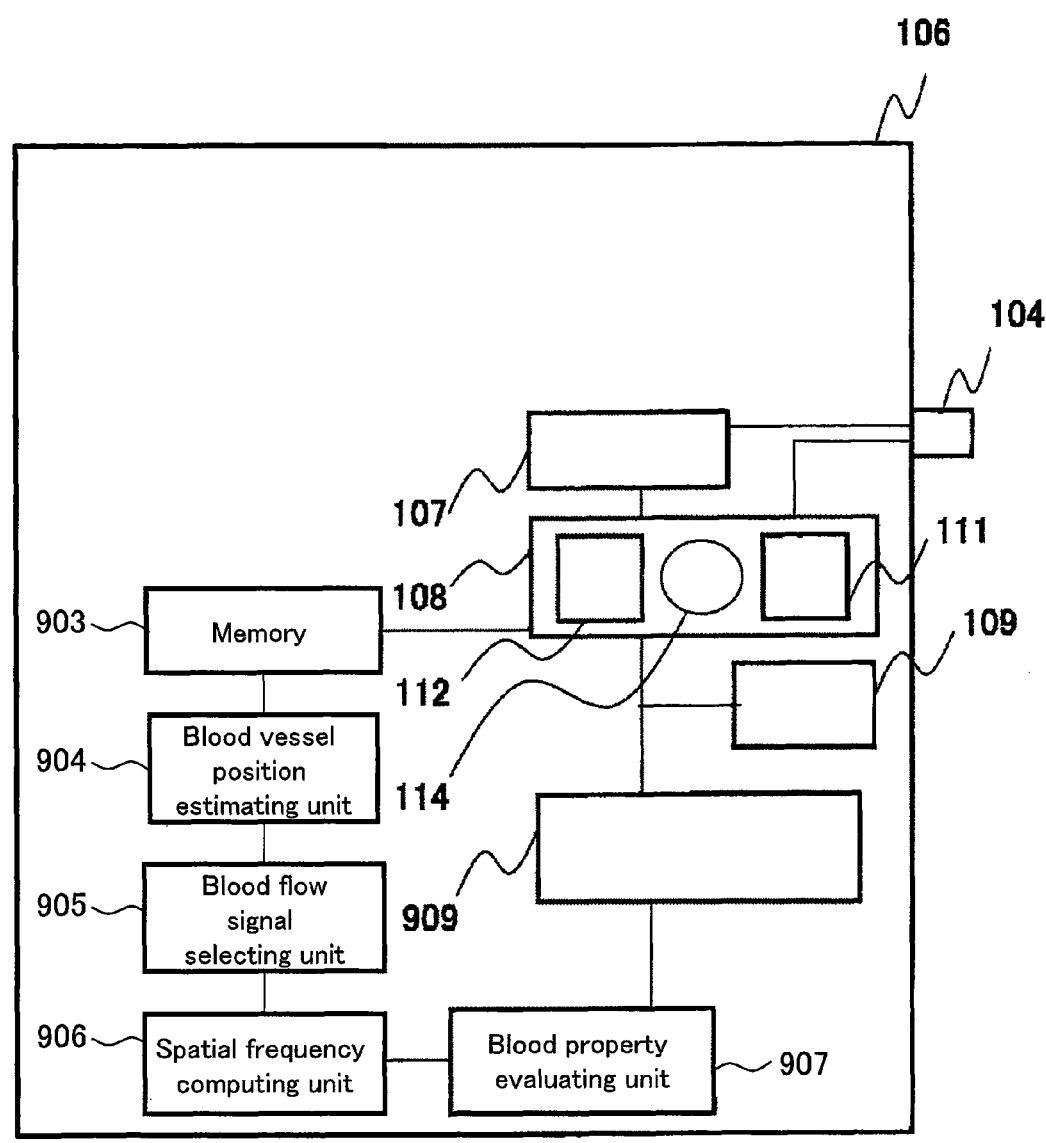
FIG. 13 shows an example of the apparatus configuration.

In a third embodiment, only the A-mode is used in the ultrasonic imaging. FIG. 13 shows a configuration of an apparatus of the third embodiment. The apparatus configuration of the third embodiment is similar to that of the second embodiment except that the raster control unit and the A/B-mode switching unit are eliminated. FIG. 10 shows the flowchart of the third embodiment. When only the A-mode is used, one ultrasonic transducer and one associated control and signal processing circuit can be used to realize the miniaturization, low power consumption, and low cost of the apparatus. On the other hand, the disadvantage due to the fact that the plural channels are not provided is that the blood vessel position is hardly estimated. The method of the second embodiment can be adopted in order to respond to the problem. Additionally, because the B-mode is not incorporated, the miniaturization, low power consumption, and low cost of the apparatus can be realized.

When the depth-direction blood vessel position estimating method is adopted in the first embodiment, the blood vessel position specifying process can be automated although the operator performs the blood vessel position specifying process in the first embodiment. Not only the automation facilitates the handling of the apparatus, but also the blood vessel position can be changed to improve the measurement accuracy when the blood vessel position is moved during the measurement.

Fourth Embodiment

Figure 14A:
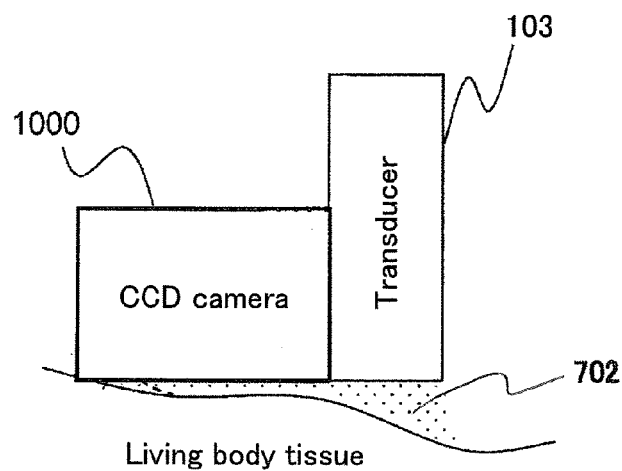
FIGS. 14A and 14B show an example of the apparatus configuration.
Figure 14B:
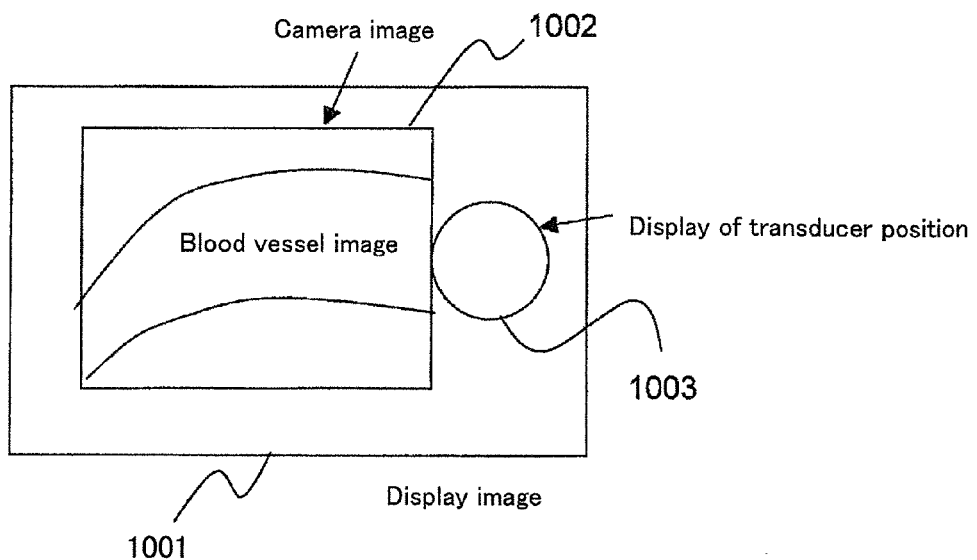

In a fourth embodiment, one-channel ultrasonic transducer and an optical scattering image are used as a method in which the positioning of the measurement is easily performed while cost is reduced. When the apparatus includes plural ultrasonic transducers and the associated control and signal processing circuits, the apparatus is enlarged or the cost is increased. On the other hand, a compact digital optical microscope having an LED light source and a CCD sensor can be realized at low cost. The hemoglobin of the blood in the living body tissue has the relatively high absorbance in the near-infrared wavelength region, and the reflection intensity of the visible light (such as green light) is high at the site where the superficial blood vessel exists. Therefore, the site where the superficial blood vessel exists can be detected. That is, the digital optical microscope is used as the blood vessel detector which is of the positioning means, and the blood vessel position is optically detected, and the ultrasonic transducer 103 is positioned according to the blood vessel position, so that the measurement can be performed by the one-channel ultrasonic transducer while the accuracy of the blood vessel position estimation is kept constant. Because the apparatus configuration of the fourth embodiment is identical to that of the third embodiment, the description thereof will not be described. FIG. 14A shows a configuration of an apparatus of the fourth embodiment. A CCD camera 1000 is fixed adjacent to the ultrasonic transducer 103. Although not shown, the brightness of the optical image can be adjusted by appropriately disposing LED around the CCD camera 1000. FIG. 14B shows a display example of the image obtained in the fourth embodiment. A camera image 1002 and an ultrasonic transducer position 1003 are displayed in a display image 1001. At this point, the blood vessel image is monitored in the camera image, and the ultrasonic transducer 103 is moved, whereby the operator can understand that the ultrasonic transducer 103 is placed at the desired position relative to the blood vessel position.

What is claimed is:

1. An ultrasonic measuring system comprising:
an ultrasonic radiation unit for radiating a test specimen with an ultrasonic signal;
a reception unit configured to receive an ultrasonic response from said test specimen;
an image data processing unit configured to produce a plurality of pieces of image data based on the ultrasonic response received by said reception unit;
a pressure applying unit configured to apply pressure to said test specimen,
a signal selecting unit configured to extract image data including a first image and a second image from the image data produced with the image data processing unit, wherein each of the first and second images represents an area of blood flow which occupies an inside of a venous blood vessel of said test specimen;
a calculating unit configured to perform a Fourier transform respectively on the image data of the first image representing the said area of the blood flow in a pressed state in which a pressure is applied on the blood vessel to stop the blood flow and on the image data of the second image representing the area of the blood flow immediately after the pressure is released; and
an evaluation unit configured to evaluate blood flow velocity of said specimen based on a difference between a skirt portion at a high frequency side of a first spatial frequency distribution which is represented in a first Fourier transform result for the image data of the first image and a skirt portion at a high frequency side of a second spatial frequency distribution which is represented in a second Fourier transform result for the image data of the second image.

2. The ultrasonic measuring system according to claim 1, further comprising a display unit configured to display evaluation information performed by said evaluation unit.

3. The ultrasonic measuring system according to claim 1, wherein said image data processing unit is further configured to produce B-mode image data as the image data.

4. The ultrasonic measuring system according to claim 1, wherein said image data processing unit is further configured to produce A-mode image data as the image data.

5. The ultrasonic measuring system according to claim 1, wherein said image data is A-mode image data including a plurality of packets, and said signal selecting unit divides said plurality of packets into temporally fluctuating packet data and temporally non-fluctuating packet data to extract the image data representing the area of blood flow.

6. The ultrasonic measuring system according to claim 1, further comprising a blood vessel detector configured to detect a position of said blood vessel.

7. The ultrasonic measuring system according to claim 6, wherein said blood vessel detector is a digital optical microscope.

8. The ultrasonic measuring system according to claim 1, wherein said evaluation unit is configured to evaluate the blood viscosity of said specimen by comparing signal components of said first image within a range from $1/60\ \mu m^{-1}$ to $1/8\ \mu m^{-1}$ with signal components of said second image within a range from $1/60\ \mu m^{-1}$ to $1/8\ \mu m^{-1}$.

* * * * *